United States Patent
Smith

(10) Patent No.: US 7,972,633 B2
(45) Date of Patent: Jul. 5, 2011

(54) NUTRITIONAL SUPPLEMENTS FOR HEALTHY MEMORY AND MENTAL FUNCTION

(75) Inventor: Kyl L. Smith, Corinth, TX (US)

(73) Assignee: Applied Cognitive Sciences, LLC, Corinth, TX (US)

(*) Notice: Subject to any disclaimer, the term of this patent is extended or adjusted under 35 U.S.C. 154(b) by 447 days.

(21) Appl. No.: 12/027,652

(22) Filed: Feb. 7, 2008

(65) Prior Publication Data

US 2008/0213401 A1  Sep. 4, 2008

Related U.S. Application Data

(60) Provisional application No. 60/899,893, filed on Feb. 7, 2007.

(51) Int. Cl.
- *A01N 65/00* (2009.01)
- *A61K 33/22* (2006.01)
- *A61K 8/67* (2006.01)
- *A61K 38/00* (2006.01)
- *C07D 213/78* (2006.01)

(52) U.S. Cl. ........ 424/725; 424/657; 562/104; 514/904; 514/17.5

(58) Field of Classification Search .................. None
See application file for complete search history.

(56) References Cited

U.S. PATENT DOCUMENTS

| | | | |
|---|---|---|---|
| 5,886,023 A | * | 3/1999 | Otomo et al. |
| 6,451,341 B1 | * | 9/2002 | Slaga et al. |
| 6,989,376 B2 | * | 1/2006 | Watkins et al. |
| 2004/0157783 A1 | * | 8/2004 | McCaddon |
| 2005/0059727 A1 | * | 3/2005 | Nair et al. |
| 2005/0244510 A1 | | 11/2005 | Smith |

FOREIGN PATENT DOCUMENTS

| | | | | |
|---|---|---|---|---|
| CN | 1759745 A | * | 4/2006 | |
| JP | 10094382 A | * | 4/1998 | |
| JP | 2001048797 A | * | 2/2001 | |
| NZ | 530554 A | * | 4/2004 | |
| WO | WO 03/003981 A2 | | 1/2003 | |

OTHER PUBLICATIONS

Moreno, M. Clinical Therapeutics, (Jan. 2003) vol. 25, No. 1, pp. 178-193. Cognitive improvement in mild to moderate Alzheimer's dementia after treatment with the acetylcholine precursor choline alfoscerate: A multicenter, double-blind, randomized, placebo-controlled trial.*

U.S. Appl. No. 10/519,515, filed Dec. 7, 2004, Notice of Abandonment mailed Mar. 20, 2008, Smith.

* cited by examiner

*Primary Examiner* — Michele Flood
(74) *Attorney, Agent, or Firm* — Cooley LLP

(57) ABSTRACT

Compositions for supporting healthy memory and optimizing mental energy and methods for improving, preventing, and treating mental disorders or deterioration. The compositions of the invention can be formulated as nutritional or dietary supplements.

6 Claims, No Drawings

NUTRITIONAL SUPPLEMENTS FOR HEALTHY MEMORY AND MENTAL FUNCTION

CROSS-REFERENCE TO RELATED APPLICATIONS

This application claims priority to U.S. Provisional Application Ser. No. 60/899,893, entitled "Nutritional Supplement for Healthy Memory and Mental Function", filed Feb. 7, 2007. The content of this provisional application is herein incorporated by reference in its entirety for all purposes.

FIELD OF THE INVENTION

The present invention relates to nutritional supplements, and more particularly relates to nutritional supplements for adults. The invention further relates to nutritional supplements supporting healthy memory, optimizing mental energy, and/or decreasing the instances and/or severity of forgetfulness. The present invention still further relates to a method to support healthy memory and/or optimize mental energy of adult, middle-aged, and elderly individuals or to improve mental function and performance by administration of the nutritional supplement.

BACKGROUND OF THE INVENTION

Memory function gradually declines with increasing age. Coincident with a decline in memory function is a concomitant increase in the incidence of mental fatigue and forgetfulness in adult, middle aged, and elderly populations of individuals. Compromised nutritional status can contribute to impaired mental performance and, hence, declining mental function of aging individuals. Thus, there is a need to develop convenient and effective methods that augment the nutritional requirements of adult, middle aged and elderly individuals, thereby supporting healthy memory and mental function for improvements in quality of life.

SUMMARY OF THE INVENTION

In one embodiment, a composition of the invention comprises at least one alpha-amino acid or N-acyl amide or ester or salt thereof; at least one plant extract; at least one inorganic salt; at least one phospholipid; at least one compound serving as a uridine source; and at least one additional ingredient selected from the group consisting of taurine or salt thereof, dimethyaminoethanol or ester or salt thereof, inositol or a phosphatidyl derivative thereof, and mixtures thereof. In another embodiment, the composition further comprises a water-soluble vitamin.

In another embodiment, a composition of the invention comprises dimethylaminoethanol, inositol, blueberry extract, ashwagandha extract, green tea leaf extract, grape seed extract, boron citrate, N-acetyl-L-cysteine, and taurine.

In another embodiment, a composition of the invention comprises dimethylaminoethanol bitartrate, inositol, blueberry extract, ashwagandha extract, green tea leaf extract, grape seed extract, boron citrate, N-acetyl-L-cysteine, taurine, O-acetyl-L-carnitine, alpha-glycerylphosphorylcholine, phosphatidylserine, vitamin C, niacin vitamin B6, folic acid, and pantothenic acid.

In another embodiment, a composition of the invention comprises Acetyl-L-Carnitine, Alpha-Glyceryl Phosphoryl Choline, Dimethylaminoethanol, Green tea extract, L-Tyrosine, *Melissa officinalis* extract, N-Acetyl-L-Cysteine, Phosphatidylserine, Rosemary leaf, Sage extract, Uridine-5'-Monophosphate and Vinpocetine.

In another embodiment, a composition of the invention includes Acetyl-L-Carnitine in the amount of about 400 to about 2,000 mg; Alpha-Glyceryl Phosphoryl Choline in the amount of about 200 to about 2,000 mg; Dimethylaminoethanol in the amount of about 50 to about 200 mg; Green Tea Leaf Extract in the amount of about 50 to about 200 mg; L-Tyrosine in the amount of about 500 to about 1,000 mg; *Melissa officinalis* extract in the amount of about 50 to about 150 mg; N-Acetyl-L-Cysteine in the amount of about 100 to about 500 mg; Phosphatidylserine in the amount of about 50 to about 300 mg; Rosemary leaf extract in the amount of about 50 to about 200 mg; Sage extract in the amount of about 50 to about 150 mg; and Uridine-5'-Monophosphate in the amount of about 25 to about 100 mg.

In another embodiment, the composition further includes Blueberry Extract, Grape Seed Extract, Inositol, Magnesium, Niacin, Pantothenic acid, Pomegranate extract, Potassium, Vitamin B12, Vitamin B6, and Vitamin C. Preferably, the nutritional supplement includes Blueberry Extract in the amount of about 50 to about 200 mg; Grape Seed Extract in the amount of about 10 to about 100 mg; Inositol in the amount of about 50 to about 500 mg; Magnesium in the amount of about 25 to about 100 mg; Niacin as inositol hexanicotinate in the amount of about 5 to about 40 mg; Pantothenic acid in the amount of about 2 to about 20 mg; Pomegranate extract in the amount of about 50 to about 200 mg; Potassium (bicarbonate) in the amount of about 99 to about 400 mg; Vitamin B12 as methylcobalamin in the amount of about 10 to about 40 mcg; Vitamin B6 as Pyridoxal-alpha-ketoglutarate in the amount of about 2 to about 20 mg; and Vitamin C as magnesium ascorbate, potassium ascorbate, and ascorbyl palmitate in the amount of about 40 to about 400 mg.

In another embodiment, the composition further includes fruit powders. Fruit powders refers to powders prepared from dehydrated fruit. Such powders may be obtained from RFI Ingredients, located in Blauvelt, N.Y. Non-limiting examples of fruit powders and representative amounts include Acai juice powder in the amount of about 500 to about 2,000 mg; Blueberry powder in the amount of about 500 to about 2,000 mg; Raspberry powder in the amount of about 250 to about 1,000 mg; and Strawberry powder in the amount of about 250 to about 1,000 mg. In another embodiment, the composition may include vegetable powders.

In another embodiment, the composition further includes D-ribose in the amount of about 2,000 to about 5,000 mg; Whey protein in the amount of about 10 to about 25 grams; Medium chain triglycerides in the amount of about 5 to about 15 grams; Isoflavones from soy or red clover in the amount of about 40 to about 100 mg; Lignans as 7-hydroxymatairesinol in the amount of about 10 to about 30 mg; and Vinpocetine in the amount of about 10 to about 40 mg.

In yet another embodiment, the invention provides a method of supporting healthy memory and optimizing mental energy or to improve mental function and performance of an individual comprising formulating the dietary supplement and administering the dietary supplement to the individual.

The various embodiments of the compositions of the invention described herein provide one or more advantages, including an alternative and improved nutritional supplement that can conveniently be used to support healthy memory function, optimize mental energy and decrease the instances, severity of forgetfulness in adult, middle aged and elderly individuals, as well as any of the other advantages associated with the individual ingredients described herein. Thus, administration of the nutritional supplement of the present invention can potentially augment the nutritional requirements of adult, middle aged, and elderly individuals, thereby supporting healthy memory, mental function and mental energy while decreasing the instances and severity of forgetfulness in individuals, in particular adult, middle-aged, and elderly individuals.

DETAILED DESCRIPTION OF THE PREFERRED EMBODIMENTS

The following description includes information that may be useful in understanding the present invention. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The composition of this invention includes a combination of unique, neurologically active nutrients, vitamins, phytochemicals and micronutrients that were specifically chosen and combined according to their biological activities.

Each nutritional component is well characterized and has been used individually to significantly improve cognitive performance in healthy subjects, as well as for the treatment and remediation of various cognitive dysfunctions. Some of the nutritional components are also known to improve metabolic dysfunctions that otherwise may lead to various disease processes.

As used here, the term "alpha-amino acid" includes primary, secondary, and tertiary amines, and the acid moiety refers to carboxylic acid. The methylene separating the amino and carboxylic acid moieties may be unsubstituted, monosubstituted, or disubstituted. Derivatives of alpha-amino acids can include N-acyl amides, esters, and carboxylate salts.

As used herein, the term "plant extract" includes vegetable extracts, herbal extracts, fruit extracts, root extracts, leaf extract, and seed extracts.

O-Acetyl-L-carnitine (or ALCAR, the biologically active form of the amino acid derivative L-carnitine) protects cells throughout the brain and body against age-related degeneration. O-Acetyl-L-carnitine is a γ-amino acid with a quaternary amine and acetylated hydroxyl group. ALCAR research, which has largely focused on the brain, has demonstrated significant improvements in mood, memory, and cognition. Studies reveal that this amino acid acts to directly improve brain health through a variety of protective mechanisms. ALCAR is so powerfully beneficial for the brain that researchers at Stanford University School of Medicine have concluded: "ALCAR slows the progression of Alzheimer's disease in younger subjects."

ALCAR is important for optimal brain function for several reasons: ALCAR is readily converted into acetylcholine, a neurotransmitter that is critical for focus, concentration, memory and learning; ALCAR is a neuronal protector and energizer, and is essential for energy production at the mitochondria; ALCAR protects brain cells from stress by protecting them against the damaging effects of the stress hormone and neurotoxin cortisol; And ALCAR can improve mental energy, performance, memory, mood, and protect the brain from age-related damage.

A substantial body of research shows that ALCAR: Provides significant protection to mitochondria and brain lipids; Reduces the build-up of cellular debris that interferes with brain function; Provides precursors necessary for acetylcholine production; Multiple studies show large mental improvements in Alzheimer's and other senile patients when supplemented; Slows the progression of Alzheimer's disease in younger subjects; Significantly benefits mild dementia; Shows significant value for interventions early in the course of dementia, before irreversible brain damage occurs; Improves normal cognition in healthy individuals; And alleviates depression in elderly individuals. In one embodiment of the compositions of the invention, ALCAR may be present in an amount ranging from about 400 to about 2,000 mg. In another embodiment, ALCAR may be present in an amount ranging from about 500 to about 2,000 mg. In another embodiment, ALCAR may be present in an amount ranging from about 500 to about 750 mg.

Alpha-Glyceryl Phosphoryl Choline (or GPC) demonstrates significant improvements in mental function in both healthy and diseased individuals. A review by an Italian research group found that, in addition to bolstering the mental performance of patients with neurodegenerative disease, GPC can enhance general mental performance in elderly subjects. A common alternative name for GPC is glycerophosphocholine.

In the elderly, GPC improves mental performance and provides noticeable mental restoration. In more than 10 clinical trials with over 1,500 participants, 'memory,' 'attention,' and other cognitive measures were shown to improve. In addition, mood (including irritability and emotional stability) improved, and patients often developed renewed interest in relatives and friends. Overall, GPC has been well tolerated, with no negative or harmful drug interactions.

One large trial in a group of elderly subjects with mild to moderate Alzheimer's dementia, published in 2003, concluded that GPC provided significant benefits for these individuals. The researchers overseeing the trial noted that the GPC patients improved not only in the realm of cognition, but in behavior and daily living activities as well. By early 2001, over 4,054 patients had been involved in published clinical trials that studied the benefits of GPC. Many of these clinical studies have investigated GPC's effects on conditions associated with dementia disorders. Some of these well-controlled trials compared the efficacy of GPC to either a placebo or a reference drug. An overall review of the combined studies at that time showed that GPC provided consistent and significant improvements in mental performance.

In two controlled trials, GPC benefited immediate recall and attention in a group of young adult males (ages 19-38) in comparison to a control group given a placebo. In middle-aged and elderly subjects, GPC has been shown to benefit or improve reaction time and improve energy generation and electrical coordination across the brain. In one embodiment of the compositions of the invention, GPC may be present in an amount ranging from about 200 to about 2,000 mg. In another embodiment, GPC may be present in an amount ranging from about 500 to about 2,000 mg.

In another embodiment, the composition of the present invention further comprises a stabilizer. The stabilizer may be present, for example, to stabilize hygroscopic ingredients (e.g., GPC). Non-limiting examples of stabilizers include mineral salts (e.g., magnesium citrate or calcium phosphate), silicon dioxide, medium chain triglycerides, and mixtures thereof.

Dimethylaminoethanol (DMAE) is found within the human brain and is a known precursor of the neurotransmitter acetylcholine and the neuronal membrane component phosphatidylcholine. DMAE has been observed to accelerate the synthesis of phosphatidylcholine, and its incorporation into neuronal cell membranes. Within the brain, DMAE has antioxidant activity: more specifically, it acts as a potent intramembrane scavenger of hydroxyl free radicals while stimulating oxidative metabolism in the cerebral cortex. Elderly patients with depression, irritability, anxiety, and lack of motivation have exhibited improvements in these clinical conditions after four weeks of supplementation. In certain embodiments of the compositions of the invention, DMAE may be present in an amount ranging from about 50 to about 200 mg. As used herein, the weight of DMAE refers to the weight of the free amine and does not take into account the weight of the counterion in the DMAE-salt complex. Common alternative names for DMAE include deanol, dimethylaminoethanol, 2-(dimethylamino)ethanol, beta-dimethylaminoethyl alcohol, and N,N-dimethyl-2-hydroxy ethylamine.

Green tea extract concentrates the known active constituents polyphenols (catechins) and flavonols. As antioxidants, research suggests polyphenols play significant roles in the prevention of chronic diseases in man, including Alzheimer's (AD) and Parkinson's disease (PD). In the case of AD, evidence in an animal model demonstrates that polyphenols decrease production of the AD related protein, beta-amyloid. In PD recent studies have demonstrated that polyphenols extracted from green tea can inhibit the uptake of dopamine and thereby, improve dopamine neurotransmission, as well as protect dopaminergic neurons from injury.

Many lines of evidence suggest that oxidative stress resulting in reactive oxygen species (ROS) generation and inflammation play a pivotal role in the age-associated cognitive decline and neuronal loss in neurodegenerative diseases. A cardinal chemical pathology observed in neurodegeneration is the accumulation of iron at sites where neurons die. The buildup of an iron gradient in conjunction with ROS (superoxide, hydroxyl radical and nitric oxide) are thought to constitute a major trigger in neuronal toxicity and demise in neurodegenerative disease. Thus, promising future treatment of neurodegenerative diseases depends on availability of effective brain permeable, iron-chelatable/radical scavenger neuroprotective ingredients that would prevent the progression of neurodegeneration. Green tea polyphenols have been reported to possess potent iron-chelating, radical-scavenging and anti-inflammatory activities and to protect neuronal death in a wide array of cellular and animal models of neurological diseases. Polyphenols have demonstrated an ability to induce neuroprotection and neurorescue in vitro and in vivo. In particular, polyphenols exhibit transitional metal (iron and copper) chelating properties and inhibition of oxidative stress. In certain embodiments of the compositions of the invention, green tea extract may be in an amount ranging from about 50 to about 200 mg and preferably comprises 98% Polyphenols/45% EGCG (Epigallocatechin Gallate).

L-tyrosine can be converted by neurons in the brain to dopamine and norepinephrine (noradrenaline), hormones which are depleted by stress, overwork and certain drugs. By replenishing norepinephrine in the brain, mental energy levels are enhanced. In addition, research suggests the conversion step from L-tyrosine to norepinephrine is enhanced in the presence of the cofactors vitamin B6 and vitamin C. The amino acid l-tyrosine has been shown to significantly improve mental performance and memory and reduce mental fatigue during times of stress. In certain embodiments of the compositions of the invention, L-tyrosine may be present in an amount ranging from about 500 to about 1,000 mg.

*Melissa officinalis* extract (Lemon balm) has traditionally been attributed with memory-enhancing properties. Analytically *M. officinalis* exhibits acetylcholinesterase inhibition. A recent study has shown that this plant modulates mood and cognitive performance when administered to young, healthy volunteers. In addition, a parallel, randomized, placebo-controlled study assessed the efficacy and safety of *M. officinalis* in patients with mild to moderate AD. The results revealed that patients receiving *M. officinalis* extract experienced significant improvements in cognition after 16 weeks of treatment. In certain embodiments of the compositions of the invention, *Melissa officinalis* extract may be present in an amount ranging from about 50 to about 150 mg.

N-Acetyl-L-Cysteine (NAC) is one of the most well-documented and effective detoxification agents known to modern nutritional science. NAC is one of the few substances that can effectively raise blood glutathione levels when taken orally and glutathione serves as the body's most potent toxin neutralizer and as the most abundant endogenous antioxidant in both the brain and body. Glutathione is central to antioxidant defenses in the brain and is an important component of cellular detoxification. In addition, NAC has been shown to significantly increase mitochondrial energy production and restore optimal mitochondrial activity. In one embodiment of the compositions of the invention, NAC may be present in an amount ranging from about 100 to about 500 mg. In another embodiment, NAC may be present in an amount ranging from 125 to about 500 mg.

Phosphatidylserine (PS) is incorporated into neuronal cell membranes, influencing the metabolism of the neurotransmitters acetylcholine, norepinephrine, serotonin, and dopamine. Researchers have suggested that phosphatidylserine enhances the processes associated with learning and consolidation of new information into memory, as well as assisting with the retrieval of that information when required. In individuals exhibiting substantial impairments—but who do not meet the criteria of dementia —PS has been shown to significantly improve learning, memory, attention, concentration, and other cognitive functions. PS generally derives from two sources: bovine brain cortex and soy lecithin.

In both placebo-controlled randomized double-blind trials and open-label trials evaluating the efficacy of PS, nearly all investigators have reported: Improved ability to perform tasks dependent on short-term memory; Increased attention span and ability to concentrate; Accelerated learning rate; Enhanced vocabulary skills; Increased ability to recall words; And increased social initiation and participation. The participants typically exhibit symptoms of mild to severe progressive memory loss and deterioration of cognitive functions (such as losses in attention, concentration, learning ability, and ability to perform daily activities) but without dementia. Beneficial effects of supplemental PS on memory also have been observed in normal elderly men and women between the ages of 50 and 75 years without symptoms or signs of cognitive impairment. In one embodiment of the compositions of the invention, PS may be present in the composition in an amount ranging from about 50 to about 300 mg and preferably derives from non-GMO (genetically modified organism) soy. In another embodiment, PS may be present in an amount ranging from 50 to 200 mg.

Cytidine-5'-diphosphocholine (CDP-choline) is a donor of choline which is used in the synthesis of both phosphatidyl choline, an important brain phospholipid, and the important neurotransmitter acetylcholine. Oral administration of CDP-choline also reactivates brain mitochondrial ATPases and the Na/K ATPases. CDP-choline plays a major role in the synthesis of phosphatidyl choline, thus protecting the integrity of neuronal cell membranes, membrane function and repair mechanisms. In certain embodiments of the compositions of the invention, CDP-Choline may be present in an amount ranging from about 25 to about 1000 mg.

Rosemary leaf extract contains rosemarinic and carnosic acids among a myriad of phenolic di- and tri-terpenoids exhibiting lipid and water-soluble antioxidant activity in aqueous systems. Carnosic acid is a potent antioxidant that possesses the unique capability of progressing through several stages of oxidation while continuing to quench ROS (the "carnosic acid cascade"). Studies have shown that carnosic acid also stimulates Nerve Growth Factor (NGF) synthesis and may be a treatment modality for Alzheimer's Disease. NGF is a nerve cell growth agent that can help counter the nerve cell damage and death caused by Alzheimer's. In certain embodiments of the compositions of the invention, Rosemary leaf extract may be present in an amount ranging from about 50 to about 200 mg.

Sage extract (*Salvia officinalis* and *Salvia lavandulaefolia*) has a longstanding reputation in British herbal encyclopedias as an agent that enhances memory. Multiple experiments utilizing a placebo-controlled, double-blind, balanced, crossover methodology showed significantly improved immediate word recall providing what researchers called: "systematic evidence that Salvia is capable of acute modulation of cognition in healthy young adults." In another study of healthy volunteers, objective measures identified significant improvements in memory while participants reported 'mood' was consistently enhanced, with increases in self-rated 'alertness,' 'calmness,' and 'contentedness,' following the active product. These results represent further evidence that Salvia is capable of acute modulation of mood and cognition in healthy young adults. Sage extracts possess anti-oxidant and anti-inflammatory properties, and specifically inhibit butyryl- and acetyl-cholinesterase. Acute administration has also been found to reliably improve mnemonic performance in healthy young and elderly cohorts, whilst a chronic regime has been shown to attenuate cognitive declines in sufferers from Alzheimer's disease. In certain embodiments of the compositions of the invention, Sage extract may be present in an amount ranging from about 50 to about 150 mg.

Uridine-5'-monophosphate (UMP) is a phosphatide building block of RNA-DNA that is critical to optimal brain function and the health of neuronal cell membranes. Membrane phospholipids like phosphatidylcholine (PC) are required for cellular growth and repair, and specifically for synaptic function. UMP enhances membrane phosphatide production and modulates at least two membrane-dependent processes—neurotransmitter release and neurite outgrowth. UMP and choline demonstrate synergistic activity as a combination of UMP and choline administration improved selective attention and spatial learning in mammals. In certain embodiments of the compositions of the invention, UMP may be present in an amount ranging from about 25 to about 100 mg.

Vinpocetine has a potent ability to reduce levels of ROS and significantly improves memory, increased cerebral blood flow, and protected the hippocampus (the memory center of the brain) in animal studies. Vinpocetine research shows: Increased glucose uptake and utilization and improved energy production in neurons; Increased activity of neurons in the hippocampus in animals; Possible improvements in long-term memory by enhancing long-term potentiation in hippocampal neurons; Protection against neuron excitotoxicity; May protect brain tissue from oxidative stress and neurotoxcity caused by beta-amyloid; Acts as a cerebral vasodilator thereby increasing cerebral blood flow, glucose uptake, oxygen utilization and intracellular energy potential; Similar cerebral vasodilating effects have been observed in adults with cerebrovascular diseases given vinpocetine.

In a controlled randomized clinical trial, patients with mild to moderate transient or permanent impairment of cognitive performance were given vinpocetine (10 or 20 mg three times a day for 16 weeks). The vinpocetine group experienced significant improvements in concentration, memory, and reduced severity of illness when compared to individuals given a placebo. When administered short-term, vinpocetine has been shown to produce beneficial effects in healthy adults who have no evidence of cerebral dysfunction. Research shows that even two days' worth of supplementation with 10, 20 or 40 mg daily increased ability to distinguish discrete sensory data, reduced reaction time, and enhanced short-term memory functions (retention and recall) to significantly greater extent than placebo. In certain embodiments of the compositions of the invention, Vinpocetine may be present in an amount ranging from about 10 to about 40 mg.

Huperzine A is an alkaloid isolated from the Chinese herb, *Huperzia serrata* that demonstrates significant and potent inhibition of the enzyme acetylcholinesterase (AChE). Huperzine A has been shown to be highly bioavailable after oral supplementation in humans and to subsequently penetrate the blood-brain barrier, accounting for its ability to stimulate an "alert" electroencephalographic pattern. In addition to enhancement of cognitive function via selective ACHE inhibition, huperzine A has been shown to attenuate glutamate-induced intracellular calcium hypermobilization in the presence of high ("excitotoxic") concentrations of glutamate and to reduce the incidence of glutamate excess-induced neuronal cell death in cell cultures. In certain embodiments of the compositions of the invention, Huperzine A may be present in an amount ranging from about 10 to about 500 mcg.

Blueberries are a potent source of high ORAC (Oxygen Radical Absorbance Capacity) antioxidants and flavonoid polyphenols. Both experimental and epidemiological evidence demonstrate that flavonoid polyphenols from green tea and blueberries improve age-related cognitive decline and are neuroprotective in models of PD, AD and cerebral ischemia/reperfusion injuries. The consumption of blueberries results in significantly enhanced short-term memory and improve measurements of learning on several cognitive performance tests. Research suggests that blueberries may be beneficial in the prevention of age-related memory deficits and enhanced cognitive performance. Researchers at Tufts University found that short-term blueberry feeding resulted in improved protection against a number of neurodegenerative processes in the ageing brain. In certain embodiments of the compositions of the invention, Blueberry extract may be present in an amount ranging from about 50 to about 200 mg.

Grape Seed Extract is composed mostly of flavan-3-ol dimmers, trimers and tetramers of catechins and epicatechins containing multiple unsaturated cyclic substructures that can serve as free electron receptors. Ultimately, grape seed proanthocysniduns are 10 to 20 times more potent than vitamin E preventing the formation of ROS. Identified polyphenolic constituents of mixtures of grape seed proanthocyanidins known to have antioxidant activity include epicatechin, epigallocatechin, epigallocatechin gallate, quercetin, myricetin, caffeic acid, ferullic acid and other phenoldienones. In one embodiment of the compositions of the invention, Grape seed extract may be present in an amount ranging from about 10 to about 100 mg and preferably comprises 95% Proanthocyanidins. In another embodiment, Grape seed extract may be present in an amount ranging from 25 to about 100 mg.

Inositol is a ubiquitous constituent of human cells. In the brain, free inositol is incorporated into neuronal cell membranes. Within neuronal cell membranes, a mixture of phosphatidylinositol plays physically and chemically integral roles in the initiation of the postreceptor intracellular "second messenger" cascade of intercellular communication and signal transduction. A series of subsequent phosphorylation reactions results in the release of neurotransmitter molecules from the presynaptic membrane. Neurotransmitters whose receptors interact with phosphatidylinositols to trigger second messenger cascades include acetylcholine, serotonin, dopamine, epinephrine and glutamine. In one embodiment of the compositions of the invention, inositol may be present in the composition in an amount ranging from about 50 to about 500 mg. In another embodiment, inositol may be present in an amount ranging from about 25 to about 100 mg. As used herein, the amount of inositol specified refers to the total amount of inositol in the composition, if it is present, for example, alone and/or in a complex with another ingredient. As used herein, the term inositol refers to one or more forms of inositol, including, for example, any form of free inositol, phosphatidyl inositol, or myo-inositol.

Magnesium is the fourth most abundant element in the brain where it plays an essential role in the regulation of central nervous system excitability. Sufficient extracellular magnesium must be available for the transmission of neural impulses and magnesium-dependent enzymes are involved in all stages of presynaptic and postsynaptic neurotransmitter function. Magnesium deficiency is associated with irritability, agitation, anxiety, confusion, depression, loss of appetite, insomnia and hyperexcitability. Inadequate magnesium intake exhibited as below-norm plasma magnesium concentrations have been associated with reduced synthesis of dopamine. In one embodiment of the compositions of the invention, magnesium may be present in an amount ranging from about 25 to about 125 mg. In another embodiment, magnesium may be present in an amount ranging from about 25 to about 100 mg.

Niacin is located in the nerve cell membranes, where it helps facilitate impulse transmission, as well as inside brain cells, where it is involved in metabolism and oxygen supply. Research has substantiated that cognitive decline, dementia, and AD can be caused by chronic niacin insufficiency. In a study examining whether dietary intake of niacin was associated with incident (AD) and cognitive decline, a large prospective study reviewed the diets of 6,158 residents aged 65 years and older. Researchers found that niacin intake had a protective effect on development of AD and cognitive decline. In one embodiment of the compositions of the invention, niacin may be present in the form of inositol hexanicotinate in an amount ranging from about 5 to about 40 mg. In another embodiment, niacin may be present in the form of inositol hexanicotinate in an amount ranging from about 10 to about 40 mg.

Pantothenic acid (vitamin B5) is a key nutrient for neuroprotection. Pantothenic acid is converted into pantethine, which in turn serves as a substrate for the synthesis of Coenzyme A (CoA). CoA improves brain function by promoting the synthesis of acetylcholine. Metabolites of CoA enhance brain metabolism and energy production through essential roles in the Krebs cycle. In order for oral GPC to increase the levels of acetylcholine, several other co-factors are involved such as pantothenic acid (vitamin B5) and methylation-enhancing nutrients such as folic acid, B12 and trimethylglycine (TMG). In one embodiment of the compositions of the invention, pantothenic acid may be present in an amount ranging from about 2 to about 20 mg. In another embodiment, pantothenic acid may be present in an amount ranging from about 5 to about 20 mg.

Pomegranates contain very high levels of antioxidant polyphenolic substances as compared to other fruits and vegetables. Polyphenols have been shown to be neuroprotective in different model systems. Pomegranate juice has been shown to significantly improve learning and memory in an animal model. Animals treated with Pomegranate had significantly less (approximately 50%) accumulation of soluble beta-amyloid deposition in the hippocampus as compared to controls. In certain embodiments of the compositions of the invention, pomegranate extract may be present in an amount ranging from about 50 to about 200 mg.

Vitamin B12 (cobalamin) is a water-soluble vitamin that is widely distributed throughout the human body and is required for facilitation of most methylation reactions, including synthesis of serotonin, dopamine and norepinephrine. Classic vitamin B12 deficiency is marked by confusion, memory impairment and cognitive deterioration. Among cohorts of healthy elderly men, those with the lowest plasma vitamin B12 concentrations exhibited the poorest memory skills. The normally aging human brain is characterized by psychomotor slowing, decreased performance on memory tasks, and reduced flexibility in thought and action. These changes are accompanied by increased monoamine oxidase activity, resulting in accelerated turnover and decreased availability of the neurotransmitters dopamine (in the striatum) and norepinephrine (in the locus ceruleus and substantia nigra). The nigro-striatal system may be especially vulnerable to "life long wear and tear" resulting from the accumulation of reactive oxygen species produced during oxidation of dopamine by monoamine oxidase. Interestingly, supplemental vitamin B12 has been reported to inhibit monoamine oxidase activity in older adults, potentially contributing to enhanced cognition via prolongation of neurotransmitter half-life and slowing the course of nigro-striatal brain dysfunction. In certain embodiments of the compositions of the invention, vitamin B12 may be present in the form of methylcobalamin in an amount ranging from about 10 to about 40 mcg.

Vitamin B6 is required for the synthesis of the neurotransmitters dopamine and serotonin, and deficiency in this vitamin results in dopamine and serotonin deficiencies and often accompanies clinical depression. Research suggests insufficient vitamin B6 intake may impair memory. Among a cohort of elderly men, those with the greatest plasma vitamin B6 concentrations exhibited the best performance on a battery of memory-dependent tests. Even healthy and apparently well-nourished elderly men without clinical depression responded to supplemental vitamin B6 with greater improvements in the storage of information in long-term memory than resulted from a placebo. In one embodiment of the compositions of the invention, vitamin B6 may be present in the form of Pyridoxal-alpha-ketoglutarate in an amount ranging from about 2 to about 20 mg. In another embodiment, vitamin B6 may be present in the form of Pyridoxal-alpha-ketoglutarate in an amount ranging from about 5 to about 20 mg.

Vitamin C is an antioxidant vitamin that has been shown to prevent neurotoxicity (excitotoxicity) following glutamate-induced intracellular depletion of glutathione by maintaining intracellular antioxidant capacity. Similarly, chemically-induced lipoperoxidation in the mouse brain has been prevented by supplemental feeding with vitamin C. Performance on tests of cognitive ability by healthy elderly men and women have been reported to be better among those subjects with the greatest plasma vitamin C (ascorbate) concentrations. This finding may reflect reduction in oxidative diminishment of mental functions. In addition, adults with mild clinical depression have responded to supplemental vitamin C with significantly increased cognition and reduced symptoms of depression. In one embodiment of the compositions of the invention, vitamin C may be present in the forms of magnesium ascorbate, potassium ascorbate, and/or ascorbyl palmitate in an amount ranging from about 40 to about 400 mg. In another embodiment, vitamin C may be present in the forms of magnesium ascorbate, potassium ascorbate, and/or ascorbyl palmitate in an amount ranging from about 100 to about 400 mg.

Ashwagandha extract has also been shown to inhibit acetylcholinesterase. In an animal model, treatment with an active constituent of ashwagandha extract identified as 'withanolide' induced significant regeneration of both axons and dendrites, in addition to the reconstruction of pre- and postsynapses in the neurons," according to scientists. Common alternative names for ashwagandha extract include *Withania somnifera*, withania, Indian ginseng, Winter cherry, Ajagandha, Kanaje hindi, and Samm Al Ferakh. In one embodiment of the compositions of the invention, Ashwagandha extract may be present in an amount ranging from about 100 to about 400 mg. In another embodiment, Ashwagandha extract may be present in an amount ranging from about 50 to about 200 mg.

Isoflavone (from soy or red clover) consumption significantly improves memory in adults. Those consuming isoflavones have showed significant improvements in short-term (immediate recall of prose and 4-s delayed matching to sample of patterns) and long-term memory (picture recall after 20 min) and in mental flexibility (rule shifting and reversal). These improvements were found in both males and females. Researchers concluded, that significant cognitive improvements can arise from a relatively brief dietary intervention, and the improvements from a high isoflavone diet are not restricted to women or to verbal tasks. In other studies, those receiving isoflavone supplements showed significantly greater improvements in recall of pictures and in a sustained attention task. The groups did not differ in their ability to learn rules, but the isoflavone supplement group showed significantly greater improvements in learning rule reversals. Individuals consuming the isoflavone supplement also showed significantly greater improvement in planning tasks. In certain embodiments of the compositions of the invention, Isoflavones may be present (from soy and/or red clover) in an amount ranging from about 40 to about 100 mg.

Taurine is a conditionally essential amino acid found abundantly throughout the excitable tissues of the central nervous system, where it is thought to have a regulating influence. This amino acid is deficient in many diets and may not be sufficiently produced by the body in certain disease states. In certain embodiments of the compositions of the invention, taurine may be present in an amount ranging from about 300 to about 1,400 mg.

Stevia Extract (stevioside) is an extract of Stevia rebaudiana, a small plant native to Paraguay and Brazil. Stevioside is 250 times sweeter than table sugar, and results of short and long-term studies have shown it to be a safe supplement for the human diet. Stevia Extract has been shown to promote healthy blood sugar levels. In certain embodiments of the compositions of the invention, stevia extract may be present in an amount ranging from about 10 mg to about 200 mg.

The methods for combining the of unique, neurologically active nutrients, vitamins, phytochemicals, and micronutrients of the present invention are well known to those of ordinary skill in the art and may be accomplished at a number of commercial production laboratories around the world including, for example, Douglas Laboratories, located in Pittsburgh, Pa.

Preferably, the compositions of the present invention are administered to adult, middle aged, and elderly individuals to support healthy memory, mental function and to optimize mental energy. The compositions of the present invention are administered to the individuals by a means suitable for consumption, such as a tablet, capsule or lozenge which can be easily swallowed, chewed, or dissolved. Additionally, or alternatively, the compositions of the present invention can be formulated into a powder or liquid for convenient addition to drinks, snack foods, dairy products or other food stuffs. The compositions of the present invention can also be consumed in the form of a snack bar, carbonated drink, or effervescent powder. The compositions of the present invention preferably are consumed on a daily basis, e.g., once a day. The dietary supplement can also be consumed multiple (greater than one) times a day (e.g., up to five times a day). The number of servings administered daily can vary from day to day.

Preferably, the compositions of the present invention are prepared in a measured free powder or liquid capsule (or liquid gelcap) dosage form, however it will be understood by those skilled in the art that other dosage forms may also be suitably prepared by known methods, for example, capsules, tablets, lozenges, powders, pastes, liquids and similar dosage forms. Solid dosage forms for oral administration include caplets, capsules, tablets, pills, powders, and granules. Solid dosage forms in various embodiments of the compositions of the present invention may be created using any pharmaceutically acceptable excipient such as fillers or extenders, binders, humectants, disintegrating agents, wetting agents and lubricants. Suitable pharmaceutically acceptable excipients are described in "Remington: The Science and Practice of Pharmacy," Lippincott Williams & Wilkins, Baltimore, Md. (2000), incorporated herein by reference.

The solid dosage forms of tablets, capsules, powders and granules can be prepared with coatings and shells such as enteric coatings and other coatings well known in the pharmaceutical formulating art. They may optionally contain opacifying agents and can also be of a composition that they release the active ingredients only, or preferentially, in a certain part of the intestinal tract, optionally, in a delayed manner.

Liquid dosage forms for oral administration include pharmaceutically acceptable emulsions, solutions, suspensions, syrups and elixirs. In addition to the active ingredients, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

The compositions are preferably administered in the early morning and afternoon, for example, administration at breakfast and lunch, so as to maintain the level of active ingredients in the system of the host during time of peak mental activity throughout a given day. Preferably, the second dose is administered within 3 to 5 hours after the first dose is consumed.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

EXAMPLES

Example 1

The composition described herein provides a representative example of a nutritional supplement according to the present invention:

| | |
|---|---|
| Vitamin C (as Magnesium Ascorbate/Potassium Ascorbate/Ascorbyl Palmitate) | 50 mg |
| Niacin (as Inositol Hexanicotinate) | 10 mg |
| Vitamin B-6 (as Pyridoxal Alpha Ketoglutarate) | 5 mg |
| Folic Acid | 340 mcg |
| Vitamin B-12 (as Methylcobalamin) | 30 mcg |
| Pantothenic Acid (as d-calcium Pantothenate) | 5 mg |
| Magnesium (as Magnesium Citrate/Ascorbate) | 25 mg |
| Alpha-GlyceroPhosphoCholine (GPC) (from 800 mg stabilized L-Alpha-GlyceroPhosphoCholine) | 400 mg |
| Acetyl-L-Carnitine (ALCAR) | 500 mg |
| Phosphatidylserine (PS) | 100 mg |
| Blend of Taurine, N-Acetyl Cysteine, Blueberry Extract (fruit), Ashwagandha Extract (root), Green Tea Extract (leaf) (98% Polyphenols/45% EGCG), Inositol, Grape Extract (seed) (95% Proanthocyanidins), Dimethylaminoethanol (DMAE Bitartrate), Boron (as Boron Citrate) | 621 mg (total weight of blend) |
| Stevia extract (leaf) | 40 mg |

Other ingredients may include: Sorbitol, Rice Syrup Solids, Natural Flavors, Malic Acid, Medium Chain Triglycerides (MCT's), Xanthan Gum The composition of Example 1 can be prepared in bulk quantities, for example, as a powder and packaged into single-serving packets according to the amounts listed in Example 1.

Example 2

The composition of Example 1 can be administered, for example, according to the following instructions:

Add one single-serving packet to about 4-6 ounces of water. Stir or agitate the resulting mixture or suspension and drink with or without food. Additional servings may be desirable, in which case one or more additional packets may be prepared as drinks and administered. A wait time of about 10-20 minutes is recommended to determine whether the effects of one serving are sufficient before administering an additional serving. At least about one to three servings a day are recommended, unless otherwise instructed by a health professional. It is also recommended that this representative example according to the present invention be administered before 4:00 pm so as not to disturb natural sleep cycles.

Example 3

The composition described in Example 1 can also be prepared in bulk quantities, for example, as a liquid in capsules. The resulting dosage forms for administration can be "Liquid GelCaps" or liquid concentrates.

REFERENCES

All publications and patent applications herein are incorporated by reference to the same extent as if each individual publication or patent application was specifically and individually indicated to be incorporated by reference.

Abbati C, et al. Nootropic therapy of cerebral aging. Adv Therapy 1991; 8:268.

Aggarwal B B, Shishodia S. Suppression of the nuclear factor-kappaB activation pathway by spice-derived phytochemicals: reasoning for seasoning. Ann NY Acad. Sci. 2004 December; 1030:434-41.

Allegro L, Favaretto V, Ziliotto G. Oral phosphatidylserine in elderly patients with cognitive deterioration. An open study. Clin Trials J 1987; 24:104-108.

Alvaro D, Cantafora A, Gandin C, Masella R, Santini M T, Angelico M. Selective hepatic enrichment of polyunsaturated phosphatidylcholines after intravenous administration of dimethylethanolamine in the rat. Biochim Biophys Acta 1989; 1006:116-120.

AM, et al., CDP-choline: neuroprotection in transient forebrain ischemia of gerbils. J Neurosci Res. Dec. 1, 1999; 58(5):697-705.

Amaducci L, Crook T H, Lippi A, Bracco L, Baldereschi M, Latorraca S, Piersanti P, Tesco G, Sorbi S. Use of phosphatidylserine in Alzheimer's disease. Annals NY Acad Sci 1991; 640:245-249.

Amaducci L. Phosphatidylserine in the treatment of Alzheimer's disease: Results of a multicenter study. Psychopharmacol Bull 1988; 24:130-134.

Amenta F et al. "The cholinergic approach for the treatment of vascular dementia: evidence from pre-clinical and clinical studies." Clin Exp Hypertens. 24, 7-8:697-713, 2002.

Ames B N, Liu J. Delaying the mitochondrial decay of aging with acetylcarnitine. Ann N Y Acad Sci. 2004 November; 1033:108-16.

Andriamampandry C, Freysz L, Kanfer J N, Dreyfus H, Massarelli R. Conversion of ethanolamine monomethylethanolamine and dimethylethanolamine to choline-containing compounds by neurons in culture and by the rat brain. Biochem J 1989; 264:555-562.

Aureli T, Di Cocco M E, Capuani G, et al. Effect of long-term feeding with acetyl-L-carnitine on the age-related changes in rat brain lipid composition: a study by 31P NMR spectroscopy. Neurochem Res. 2000 March; 25(3):395-9.

Avraham Y, et al. Med Sci Sports Exerc. 2001 December; 33(12):2104-10.

Balestreri R, Fontana L, Astengo F. A double-blind placebo controlled evaluation of the safety and efficacy of vinpocetine in the treatment of patients with chronic vascular senile cerebral dysfunction. J Am Geriatr Soc 1987; 35:425-430.

Bartus R T, Dean R L, Beer B, Lippa A S. The cholinergic hypothesis in geriatric memory dysfunction. Science 1982; 217:408-417.

Bencsath P, Debreczeni L, Takacs L. Effect of ethyl apovincaminate on cerebral circulation of dogs under normal conditions and in arterial hypoxia. Arzneim-Forsch (Drug Res) 1976; 26:1920-1923.

Bielenberg G W, Hayn C, Krieglstein J. Effects of cerebroprotective agents on enzyme activities of rat primary glial cultures and rat cerebral cortex. Biochem Pharmacol 1986; 355:2693-2702.

Binienda z, Przybyla-Zawislac B, et al. 1-Carnitine and Neuroprotection in the Animal Model of Mitochondrial Dysfunction. Ann. N.Y. Acad. Sci. 1053:174-182 (2005). doi: 10.1196/annals. 1344.015.

Brooks J, Yesavage J, et al. Acetyl L-carnitine slows decline in younger patients with Alzheimer's disease: a reanalysis of a double-blind, placebo-controlled study using the trilinear approach. *Int Psychogeriatr* 1998 (Vol. 10 Issue 2) 193-203.

Brooks J O 3rd, Yesavage J A, Carta A, Bravi D. Acetyl L-carnitine slows decline in younger patients with Alzheimer's disease: a reanalysis of a double-blind, placebo-controlled study using the trilinear approach. *Int Psychogeriatr.* 1998 June; 10(2):193-203.

Bruno G, Scaccianoce S, et al. Acetyl-L-carnitine in Alzheimer disease: a short-term study on CSF neurotransmitters and neuropeptides. Alzheimer Dis Assoc Disord (Vol. 9, Issue 3):128-31.

Caffara P, Santamaria V. The effects of phosphatidylserine in patients with mild cognitive decline. An open trial. *Clin Trials J* 1987; 24:109-114.

Canal N, et al. Comparison of the effects of pretreatment with choline alfoscerate, idebenone, aniracetam and placebo on scopolamine-induced amnesia. Le Basi Raz Ter 1993; 23:102.

Canal N, et al. Effect of 1-alpha-glyceryl-phosphorylcholine on amnesia caused by scopolamine. International J Clin Pharmacol Therapy Toxicol 1991; 29:103.

Carta A, Calvani M, et al. Acetyl-L-carnitine and Alzheimer's disease: pharmacological considerations beyond the cholinergic sphere. Ann N Y Acad Sci 1993 (Vol. 695) 324-6.

Carta A, Calvani M. Acetyl-L-carnitine: a drug able to slow the progress of Alzheimer's disease? *Ann N Y Acad Sci.* 1991; 640:228-32.

Cenacchi T, Baggio C, Palin E. Human tolerability of oral phosphatidylserine assessed through laboratory examinations. *Clin Trials J* 1987; 24:125-131.

Cenacchi T, Bertoldin T, Farina C, Fiori M G, Crepaldi G. Cognitive decline in the elderly: A double blind, placebo-controlled multicenter study on efficacy of phosphatidylserine administration. *Aging Clin Exp Res* 1993; 5:123-133.

Chaudhary G, Sharma U, Jagannathan N R, Gupta Y K. Evaluation of *Withania somnifera* in a middle cerebral artery occlusion model of stroke in rats. Clin Exp Pharmacol Physiol. 2003 May; 30(5-6):399-404.

Chen H, et al. Biological and dietary antioxidants protect against DNA nitration induced by reaction of hypochlorous acid with nitrite. Arch Biochem Biophys 415(1):109-16, Jul. 1, 2003.

Choudhary M I, Yousuf S, Nawaz S A, Ahmed S, Atta uR. Cholinesterase inhibiting withanolides from Withania somnifera. Chem Pharm Bull (Tokyo). 2004 November; 52(11):1358-61.

Coleston D M, Hindmarch I. Possible memory-enhancing properties of vinpocetine. Drug Develop Res 1988; 14:191-193.

Colodny L, Hoffman R L. Inositol—clinical applications for exogenous use. *Alternative Med Rev* 1998; 3:432-447.

Coupland N, et al. J Psychiatry Neurosci. 2001 May; 26(3):247-51.

Crook T, Petrie W, Wells C, Massari D C. Effects of phosphatidylserine in Alzheimer's disease. *Psychopharmacol Bull* 1992; 28:61-66.

Crook T H, Tinklenberg J, Yesavage J, Petrie W, Nunzi M G, Massari D C. Effects of phosphatidylserine in age-associated memory impairment. Neurology 1991; 41:644-649.

Curti D, Dagani F, et al. Effect of aging and acetyl-L-carnitine on energetic and cholinergic metabolism in rat brain regions. *Mech Ageing Dev.* 1989 January; 47(1):39-45.

Dainous F, Kanfer J N. Effect of modification of membrane phospholipid composition on phospholipid methylation in aggregating cell culture. *J Neurochem* 1986; 46:1859-1864.

De Bruin N M, Kiliaan A J, De Wilde M C, Broersen L M. Combined uridine and choline administration improves cognitive deficits in spontaneously hypertensive rats. Neurobiol Learn Mem. 2003 July; 80(1):63-79.

De Jesus Moreno Moreno M. Cognitive improvement in mild to moderate Alzheimer's dementia after treatment with the acetylcholine precursor choline alfoscerate: a multicenter, double-blind, randomized, placebo-controlled trial. Clin Ther 2003; 25:178-193.

de la Torre J C. Cerebral hypoperfusion, capillary degeneration, and development of Alzheimer disease. *Alzheimer Dis Assoc Disord.* 2000; 14 (Suppl. 1):S72-S81.

De Quay B, et al. Glutathione depletion in HIV-infected patients: Role of cysteine deficiency and effect of oral N-acetylcysteine. AIDS 6:815-9, 1992.

Deijen J B, Orlebeke J F. Effect of tyrosine on cognitive function and blood pressure under stress. *Brain Res Bull.* 1994; 33(3):319-23.

Deijen J B, Wientjes C J, Vullinghs H F, Cloin P A, Langefeld J J. Tyrosine improves cognitive performance and reduces blood pressure in cadets after one week of a combat training course. Brain Res Bull. 1999 Jan. 15; 48(2):203-9.

Delwaide P J, Gyselynck-Mambourg A M, Hurlet A, Ylieff M. Double-blind randomized controlled study of phosphatidylserine in senile demented patients. *Acta Neurol Scand* 1986; 73:136-140.

DeNoble V J. Vinpocetine enhances retrieval of a step-through passive avoidance response in rats. *Pharmacol Biochem Behavior* 1987; 26:183-186.

Dhuley J N. Nootropic-like effect of ashwagandha (Withania somnifera L.) in mice. Phytother Res. 2001 September; 15(6):524-8.

Dimpfel W, Hofman H C, Prohaska A, Schober F, Schellenberg R. Source density analysis of functional topographical EEG: Monitoring of cognitive drug action. *Eur J Med Res* 1995-1996; 1:283-290.

Dollins A B, Krock L P, et al. L-tyrosine ameliorates some effects of lower body negative pressure stress. *Physiol Behav.* 1995 February; 57(2):223-30.

Dowson J. et al. The morphology of lipopigment in rat Purkinje neurons after chronic acetyl-L-carnitine administration: a reduction in aging-related changes. *Biol Psychiatry.* 1992 Jul. 15; 32(2):179-87.

Engel R R. Double-blind cross-over study of phosphatidylserine vs. placebo in subjects with early cognitive deterioration of the Alzheimer type. *Eur Neuropsychopharmacol* 1992; 2:149-155.

Erdo S L, Cai N-S, Wolff J R, Kiss B. Vinpocetine protects against excitotoxic cell death in primary cultures of rat cerebral cortex. *Eur J Pharmacol* 1990; 187:551-553.

Ferris S H, Sathananthan G, Gershon S, Clark C. Senile dementia: Treatment with Deanol. *J Am Geriatr Soc* 1977; 25:241-244.

Fischer K, Colombani P C, et al. Carbohydrate to protein ratio in food and cognitive performance in the morning. *Physiol Behav.* 2002 March; 75(3):411-23.

Fishbane S, Durham J, et al. N-Acetylcysteine In The Prevention Of Radiocontrast-Induced Nephropathy, *J Am Soc Nephrol* 15:251-260, 2004.

Geller S J. Comparison of a tranquilizer and a psychic energizer. *JAMA* 1960; 174:481-484.

Granata Q, DiMichele J. Phosphatidylserine in elderly patients. An open trial. *Clin Trials J* 1987; 24:99-103.

Groo D, Palosi E, Szporny L. Comparison of the effects of vinpocetine, vincamine, and nicergoline on the normal and hypoxia-damaged learning process in spontaneously hypertensive rats. *Drug Develop Res* 1988; 15:75-85.

Hadjiev D, Yancheva S. Rheoencephalographic and psychological studies with ethyl apovincaminate in cerebral vascular insufficiency. *Arzneim-Forsch (Drug Res)* 1976; 26:1947-1950.

Hagiwara M, Endo T, Hidaka H. Effects of vinpocetine on cyclic nucleotide metabolism in vascular smooth muscle. *Biochem Pharmacol* 1984; 33:453-457.

Heiss W D, Kessler J, Mielke R, Szelies B, Herholz K. Long-term effects of phosphatidylserine, pyritinol, and cognitive training in Alzheimer's disease. *Cognitive Deterioration* 1994; 5:88-98.

Heiss W-D, Szelies B, Kessler J, Herholz K. Abnormalities of energy metabolism in Alzheimer's disease studied with PET. *Annals NY Acad Sci* 1991; 640:65-71.

Hindmarch I, Fuchs H—H, Erzigkeit H. Efficacy and tolerance of vinpocetine in ambulant patients suffering from mild to moderate organic psychosyndromes. *Internat Clin Psychopharmacol* 1991; 6:31-43.

Hoozemans J J, Veerhuis R, Janssen I, et al. The role of cyclo-oxygenase 1 and 2 activity in prostaglandin E(2) secretion by cultured human adult microglia: implications for Alzheimer's disease. Brain Res. 2002 Oct. 4; 951(2):218-26.

Imamoto T, Tanabe M, Shimamoto N, Kawazoe K, Hirata M. Cerebral circulatory and cardiac effects of vinpocetine and its metabolite, apovincaminic acid, in anesthetized dogs. *Arzneim-Forsch (Drug Res)* 1984; 34:161-169.

Ishihara K, Katsuki H, Sugimura M, Satoh M. Idebenone and vinpocetine augment long-term potentiation in hippocampal slices in the guinea pig. Neuropharmacol 1989; 28:569-573.

Karpati E, Szporny L. General and cerebral haemodynamic activity of ethyl apovincaminate. *Arzneim-Forsch (Drug Res)* 1976; 26:108-1912.

Kidd P M. GPC, Nutraceutical breakthrough for mental performance. Total Health 2001; 23:5556.

Kim H S, Kim M H, Jeong M, et al. EGCG blocks tumor promoter-induced MMP-9 expression via suppression of MAPK and AP-1 activation in human gastric AGS cells. Anticancer Res. 2004 March-April; 24(2B):747-53.

Kuboyama T, Tohda C, Komatsu K. Neuritic regeneration and synaptic reconstruction induced by withanolide A. Br J. Pharmacol. 2005 April; 144(7):961-71.

Kuratsune H, Yamaguti K, Lindh G, et al. Brain regions involved in fatigue sensation: reduced acetylcarnitine uptake into the brain. Neuroimage. 2002 November; 17(3):1256-65.

Lakics V, Sebestyen M G, Erdo S L. Vinpocetine is a highly potent neuroprotectant against vertridine-induced cell death in primary cultures of rat cerebral cortex. *Neurosci Lett* 1995; 185:127-130.

Lakics V, Sebestyen M G, Erdo S L. Vinpocetine is a highly potent neuroprotectant against vertridine-induced cell death in primary cultures of rat cerebral cortex. *Neurosci Lett* 1995; 185:127-130.

Lewis J A, Young R. Deanol and methylphenidate in minimal brain dysfunction. *Clin Pharmacol Ther* 1975; 17:534-540.

Lino A, Boccia M, et al. Psycho-functional changes in attention and learning under the action of L-acetylcarnitine in 17 young subjects. A pilot study of its use in mental deterioration. *Clin Ther.* 1992 June; 140(6):569-73.

Liu J, Atamna H, Kuratsune H, Ames B N. Delaying brain mitochondrial decay and aging with mitochondrial antioxidants and metabolites. *Overview Ann N Y Acad. Sci.* 2002 April; 959:133-66.

Liu J, Head E, et al. Memory loss in old rats is associated with brain mitochondrial decay and RNA/DNA oxidation: partial reversal by feeding acetyl-L-carnitine and/or R-alpha-lipoic acid. *Proc Natl Acad Sci USA.* 2002 Feb. 19; 99(4):2356-61.

Lo A H, Liang Y C, Lin-Shiau S Y, Ho C T, Lin J K. Carnosol, an antioxidant in rosemary, suppresses inducible nitric oxide synthase through down-regulating nuclear factor-kappaB in mouse macrophages. Carcinogenesis. 2002 June; 23(6):983-91.

Locatelli M, et al. Neurophysiological evaluation of alphaGFC (choline alfoscerate) by means of computerized electroencephalogram (CEEG). Le Basi Raz Ter 1990; 20:79.

Lohr J, Acara M. Effect of dimethylethanolamine, an inhibitor of betaine production, on the disposition of choline in the rat kidney. *J Pharmacol Exp Ther* 1990; 252:154-158.

Maggioni M, Picotti G B, Bondiolotti G P, Panerai A, Cenacchi T, Nobile P, Brambilla F. Effects of phosphatidylserine therapy in geriatric patients with depressive disorders. *Acta Psychiatr Scand* 1990; 81:265-270.

Manconi E, Binaghi F, Pitzus F. A double-blind clinical trial of vinpocetine in the treatment of cerebral insufficiency of vascular and degenerative origin. *Curr Ther Res* 1986; 40:702-709.

Medina S, et al, Antioxidants inhibit the human cortical neuron apoptosis induced by hydrogen peroxide, tumor necrosis factor alpha, dopamine and beta-amyloid peptide 1-42. *Free Radic Res* 36(11):1179-84, November 2002.

Miyamoto M, Murphy T H, Schnaar R L, Coyle J T. Antioxidants protect against glutamate-induced cytotoxicity in a neuronal cell line. *J Pharmacol Exptl Ther* 1989: 250:1132-1140.

Miyazaki M. The effect of a cerebral vasodilator, vinpocetine, on cerebral vascular resistance evaluated by the Doppler ultrasonic technique in patients with cerebrovascular diseases. *Angiology* 1995; 46:53-58.

Moglia A, Bergonzoli S, de Moliner P. Effect of a GFC in brain mapping changes in patients with age associated memory impairment (AAMI). Le Basi Razionali della Terapia, 1990; 20:83-89.

Moyers S B, Kumar N B. Green tea polyphenols and cancer chemoprevention: multiples mechanisms and endpoints for phase II trials. Nutr Rev. 2004 May; 62(5)204-11.

Neal R, et al. Antioxidant role of N-acetyl cysteine isomers following high dose irradiation. *Free Radic Biol Med* 34(6):689-95, Mar. 15, 2003.

Neri D F, Wiegmann D, et al. The effects of tyrosine on cognitive performance during extended wakefulness. *Aviat Space Environ Med.* 1995 April; 66(4):313-9.

Nicholson C D. Pharmacology of nootropics and metabolically active compounds in relation to their use in dementia. Psychopharmacol 1990; 101:147-159.

Oettinger L. The use of Deanol in the treatment of disorders of behavior in children. *J Pediatr:*671-675.

Otomo E, Atarashi J, Araki G, Ito E, Omae T, Kuzuya F, Nukada T, Ebi O. Comparison of vinpocetine with ifenprodil tartrate and dihydroergotoxine mesylate treatment and results of long-term treatment with vinpocetine. *Curr Ther Res* 1985; 37:811-821.

Palmieri G, Palmieri R, Inzoli M R, Lombardi G, Sottini C, Tavolato B, Giometto B. Double-blind controlled trial of phosphatidylserine in patients with senile mental deterioration. *Clin Trials J* 1987; 24:73-83.

Pantano P, Baron J-C, Lebrun-Grandie P, Duquesnoy N, Bousser M-G, Comar D. Regional cerebral blood flow and oxygen consumption in human aging. Stroke 1984; 15:635-641.

Parnetti L et al. Choline alphoscerate in cognitive decline and in acute cerebrovascular disease: an analysis of published clinical data. Mech Ageing Dev 2001 November: 122(16):2041-2055.

Parnetti L. Pharmacokinetics of IV and oral acetyl-L-carnitine in a multiple dose regimen in patients with senile dementia of Alzheimer type. Eur J Clin Pharmacol 1992 (Vol. 42, Issue 1) 89-93.

Passeri M, Cucinotta D, et al. Acetyl-L-carnitine in the treatment of mildly demented elderly patients. *Int J Clin Pharmacol Res.* 1990; 10(1-2):75-9.

Paulo T, Toth P T, Nguyen T T, Forgacs L, Torok T L, Magyar K. [$^3$H]Noradrenaline-releasing action of vinpocetine in the isolated main pulmonary artery of the rabbit. *J Pharm Pharmacol* 1986; 38:668-673.

Penland J G. The importance of boron nutrition for brain and psychological function. Biol Trace Elem Res. 1998 Winter; 66(1-3):299-317.

Pereira C, Agostinho P, Oliveira C R. Vinpocetine attenuates the metabolic dysfunction induced by amyloid betapeptides in PC12 cells. Free Radic Res. 2000 November; 33(5):497-506.

Petersen M, Simmonds M S. Rosmarinic acid. Phytochemistry. 2003 January; 62(2):121-5.

Pettegrew J, Klunk W, et al. Clinical and neurochemical effects of acetyl-L-carnitine in Alzheimer's disease. *Neurobiol Aging.* 1995 January-February; 16(1):1-4.

Pettegrew J, Klunk W, et al. Clinical and neurochemical effects of acetyl-L-carnitine in Alzheimer's disease. Neurobiol Aging 1995 (Vol. 16, Issue 1) 1-4.

Pettegrew J, Levine J, McClure R J. Acetyl-L-carnitine physical-chemical, metabolic, and therapeutic properties: relevance for its mode of action in Alzheimer's disease and geriatric depression. Mol Psychiatry 2000 November; 5(6):616-32.

Pillai S P, Mitscher L A, Menon S R, et al. Antimutagenic/antioxidant activity of green tea components and related compounds. J Environ Pathol Toxicol Oncol. 1999; 18(3):147-58.

Rai G, Wright G, et al. Double-blind, placebo controlled study of acetyl-1-carnitine in patients with Alzheimer's dementia. Curr Med Res Opin 1990 (Vol 11, Issue 10) 638-47.

Rischke R, Krieglstein J. Protective effect of vinpocetine against brain damage caused by ischemia. *Japn J Pharmacol* 1991; 56:349-356.

Rosdy B, Balazs M, Szporny L. Biochemical effect of ethyl apovincaminate. *Arzneim-Forsch (Drug Res)* 1976; 26:1923-1926.

Rosen M A, Jones R M, Yano Y, Budinger T F. Carbon-11 choline: Synthesis, purification, and brain uptake inhibition by 2-dimethylaminoethanol. *J Nucl Med* 1985; 26:1424-1428.

Salvioli G, Neri M. L-acetylcarnitine treatment of mental decline in the elderly. Drugs Exp Clin Res. 1994; 20(4): 169-76.

Sannita W G. Techniques of functional exploration of the SNC and models of cholinergic functioning. Le Basi Raz Ter 1993; 33:81.

Sano M, Bell K, et al. Double-blind parallel design pilot study of acetyl levocarnitine in patients with Alzheimer's disease. Arch Neurol 1992 (Vol. 49, Issue 11) 1137-41.

Sauer D, Rischke R, Beck T, Robberg C, Mennel H-D, Bielenberg G W, Krieglstein J. Vinpocetine prevents ischemic cell damage in rat hippocampus. *Life Sci* 1988; 43:1733-1739.

Schreiber S, Kampf-Sherf O, Gorfine M, Kelly D, Oppenheim Y, Lerer B. An open trial of plant-source derived phosphatidylserine for treatment of age-related cognitive decline. *Isr J Psychiatry Relat Sci* 2000; 37:302-307.

Shibota M, Kakihana M, Nagaoka A. The effect of vinpocetine on the brain glucose uptake in mice. *Folia Pharmacol Japan* 1982; 80:221-224.

Sicurella L, et al. Changes in VEP in subjects treated with alphaGFC. Preliminary study. Le Basi Raz Ter 1990; 20:91.

Sinforiani E, Agostinis C, Merlo P, Gualtieri S, Mauri M, Mancuso A. Cognitive decline in ageing brain. Therapeutic approach with phosphatidylserine. *Clin Trials J* 1987; 24:115-125.

Sinforiani E, Jannuccelli M, et al. Neuropsychological changes in demented patients treated with acetyl-L-carnitine. *Int J Clin Pharmacol Res.* 1990 (Vol. 10, Issue 1-2) 69-74.

Steffen V. Santiago, M., de la Cruz, C. P., et al., Effect of intraventricular injection of 1-methyl-4-phenylpridinium protection by acetyl-L-carnitine. Human Exp Toxicol 14:865-871, 1995.

Subhan Z, Hindmarch I. Psychopharmacological effects of vinpocetine in normal healthy volunteers. Eur J Clin Pharmacol 1985; 28:567-571.

Teather L A, Wurtman R J. Chronic Administration of UMP Ameliorates the Impairment of Hippocampal-Dependent Memory in Impoverished Rats American Society for Nutrition J. Nutr. 136:2834-2837, November 2006.

Thal L, Carta A, et al. A 1-year multicenter placebo-controlled study of acetyl-L-carnitine in patients with Alzheimer's disease. Neurology. 1996 September; 47(3):705-11.

Thal L. J., Carta A. Clarke, W. R., et al., A 1-year multicenter placebo-controlled study of acetyl-L-carnitine in patients with Alzheimer's disease. Neurology 47:705-711, 1996.

Tretter L, Adam-Vizi V. The neuroprotective drug vinpocetine prevents veratridine-induced $[Na^+]_i$ and $[Ca^{2+}]_i$ rise in synaptosomes. *NeuroReport* 1998; 9:1849-1853.

Ved H S et al., Huperzine A, a potential therapeutic agent for dementia, reduces neural cell death caused by glutamate. Neuroreport. Mar. 3, 1997; 8(4):963-8.

Vezzetti V, Bettini R. Clinical and instrument evaluation of the effect of choline alfoscerate on cerebral decline. Presse Medicale 1992; 5:141.

Villardita C, Grioli S, Salmeri G. Nicoletti F, Pennisi G. Multicentre clinical trial of brain phosphatidylserine in elderly patients with intellectual deterioration. *Clin Trials J* 1987; 24:84-93.

Virmani A, Binienda Z. Role of carnitine esters in brain neuropathology. *Mol Aspects Med.* 2004 October; 25(5-6):53349.

Wang L, Pooler A M, Albrecht M A, Wurtman R J. Dietary uridine-5'-monophosphate supplementation increases potassium-evoked dopamine release and promotes neurite outgrowth in aged rats. J Mol. Neurosci. 2005; 27(1):137-45.

White H, Scares P. Acetyl-L-carnitine as a precursor of acetylcholine. Neurochem Res. 1990 June; 15(6):597-601.

Xiong Y, Peterson P, Lee C. Effect of N-acetylcysteine on mitochondrial function following traumatic brain injury in rats. *J Neurotrauma.* 1999 November; 16(11):1067-82.

Yavin E. Polar head group decarboxylation and methylation of phospholipids: An alternate route for phosphatidylcholine formation in cultures neuronal cells. *J Neurochem* 1985; 44:1451-1458.

Zs-Nagy I, Floyd R A. Electron spin resonance spectroscopic demonstration of the hydroxyl free radical scavenger properties of dimethylaminoethanol in spin trapping experiments confirming the molecular basis for the biological effects of centrophenoxine. *Arch Gerontol Geriatr* 1984; 3:297-310.

Zs-Nagy I, Semsei I. Centrophenoxine increases the rates of total and mRNA synthesis in the brain cortex of old rats: an explanation of its action in terms of the membrane hypothesis of aging. *Exp Gerontol.* 1984; 19(3):171-8.

Zs-Nagy I. On the role of intracellular physicochemistry in quantitative gene expression during aging and the effect of centrophenoxine. A review. *Arch Gerontol Geriatr.* 1989 November-December; 9(3):215-29.

What is claimed is:

1. A composition consisting essentially of:
  a. taurine in the amount of about 300 mg to about 1,400 mg;
  b. N-acetyl-L-cysteine in the amount of about 500 to about 750 mg;
  c. blueberry extract in the amount of about 50 to about 200 mg;
  d. ashwagandha extract in the amount of about 50 to about 400 mg;
  e. green tea leaf extract in the amount of about 50 to about 200 mg;
  f. inositol is present in the amount of about 25 to about 100 mg;
  g. grape seed extract in the amount of about 25 to about 100 mg;
  h. dimethylaminoethanol in the amount of about 50 to about 200 mg;
  i. boron citrate in the amount of about1 to about 5 mg;
  j. N-acetyl-L-carnitine in the amount of about 500 to about 2,000 mg;
  k. alpha-glycerylphosphorylcholine in the amount of about 500 to about 2,000 mg;
  l. phosphatidylserine in the amount of about 50 to about 200 mg;
  m. vitamin C as a mixture of magnesium ascorbate, potassium ascorbate, and ascorbyl palmitate in the amount of about 100 to about 400 mg;
  n. niacin as inositol hexanicotinate in the amount of about 10 to about 40 mg;
  o. vitamin B6 as pyridoxal-alpha-ketoglutarate in the amount of about 5 to about 20 mg;
  p. folic acid in the amount of about 200 to about 450 mcg;
  q. pantothenic acid as d-calcium pantothenate in the amount of about 5 to about 20 mg;
  r. magnesium in the amount of about 25 to about 100 mg; and
  s. uridine-5'-monophosphate in the amount of about 25 to about 100 mg.

2. A composition consisting of:
  a. taurine in the amount of about 300 mg to about 1,400 mg;
  b. N-acetyl-L-cysteine in the amount of about 500 to about 750 mg;
  c. blueberry extract in the amount of about 50 to about 200 mg;
  d. ashwagandha extract in the amount of about 50 to about 400 mg;
  e. green tea leaf extract in the amount of about 50 to about 200 mg;
  f. inositol is present in the amount of about 25 to about 100 mg;
  g. grape seed extract in the amount of about 25 to about 100 mg;
  h. dimethylaminoethanol in the amount of about 50 to about 200 mg;
  i. boron citrate in the amount of about 1 to about 5 mg;
  j. N-acetyl-L-carnitine in the amount of about 500 to about 2,000 mg;
  k. alpha-glycerylphosphorylcholine in the amount of about 500 to about 2,000 mg;
  l. phosphatidylserine in the amount of about 50 to about 200 mg;
  m. vitamin C as a mixture of magnesium ascorbate, potassium ascorbate, and ascorbyl palmitate in the amount of about 100 to about 400 mg;
  n. niacin as inositol hexanicotinate in the amount of about 10 to about 40 mg;
  o. vitamin B6 as pyridoxal-alpha-ketoglutarate in the amount of about 5 to about 20 mg;
  p. folic acid in the amount of about 200 to about 450 mcg;
  q. pantothenic acid as d-calcium pantothenate in the amount of about 5 to about 20 mg;
  r. magnesium in the amount of about 25 to about 100 mg;
  s. optionally, uridine-5'-monophosphate in the amount of about 25 to about 100 mg; and
  t. optionally, at least one flavoring agent, at least one stabilizer, or at least one dessicant.

3. A method of improving or reducing the risk of deterioration of mental function comprising administering to a person in need thereof an effective amount of the composition of claim 1 or claim 2.

4. The method of claim 3, wherein the composition is administered one, two, three, four, or five times daily.

5. A method of treating mental deterioration or disorder comprising administering to a person in need thereof an effective amount of the composition of claim 1 or claim 2.

6. The method of claim 5, wherein said composition is administered one, two, three, four, or five times daily.

* * * * *